United States Patent
Palazzotto et al.

(10) Patent No.: US 9,506,888 B2
(45) Date of Patent: Nov. 29, 2016

(54) VAPOR SENSOR INCLUDING SENSOR ELEMENT WITH INTEGRAL HEATING

(75) Inventors: Michael C. Palazzotto, Woodbury, MN (US); Justin Tungjunyatham, Roseville, MN (US); Stefan H. Gryska, Woodbury, MN (US); Michael S. Wendland, North St. Paul, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 426 days.

(21) Appl. No.: 14/110,047

(22) PCT Filed: Apr. 4, 2012

(86) PCT No.: PCT/US2012/032153
§ 371 (c)(1),
(2), (4) Date: Oct. 4, 2013

(87) PCT Pub. No.: WO2012/141958
PCT Pub. Date: Oct. 18, 2012

(65) Prior Publication Data
US 2014/0028333 A1    Jan. 30, 2014

Related U.S. Application Data

(60) Provisional application No. 61/475,009, filed on Apr. 13, 2011.

(51) Int. Cl.
*G01R 27/26* (2006.01)
*G01N 27/22* (2006.01)
*G01N 27/12* (2006.01)

(52) U.S. Cl.
CPC .......... *G01N 27/228* (2013.01); *G01N 27/123* (2013.01); *G01N 27/227* (2013.01)

(58) Field of Classification Search
CPC . G01N 27/228; G01N 27/123; G01N 27/227
USPC ................................. 324/658–690
See application file for complete search history.

(56) References Cited

U.S. PATENT DOCUMENTS 4,638,443 A    1/1987  Kaneyasu
4,703,646 A   11/1987  Muller
(Continued)

FOREIGN PATENT DOCUMENTS

CN    1117196 A    2/1996
DE    10041921    3/2002
(Continued)

OTHER PUBLICATIONS

Budd, "Polymers of intrinsic microporosity (PIMs): robust, solution-processable, organic nanoporous materials", Chemical Communications, 2004, pp. 230-231.
(Continued)

*Primary Examiner* — Daniel Miller
(74) *Attorney, Agent, or Firm* — Yufeng Dong; Bradford B. Wright

(57) ABSTRACT

A vapor sensor includes a capacitance-related property sensor element (110), a heater circuit element (170), a capacitance-related property measurement circuit element (180), and at least one switch member (190). The capacitance-related property sensor element includes a dielectric substrate (120), a first conductive electrode (130), a second conductive electrode (140), and a layer of dielectric microporous material (150) disposed between and contacting the first conductive electrode and the second conductive electrode. The at least one switch member is capable of interrupting electrical communication between the first conductive electrode and the heater circuit element, and between the capacitance-related property measurement circuit element and the first conductive electrode.

11 Claims, 2 Drawing Sheets

(56) References Cited

U.S. PATENT DOCUMENTS

| | | |
|---|---|---|
| 4,975,249 A | 12/1990 | Elliott |
| 5,269,175 A | 12/1993 | Chmiel |
| 5,296,819 A | 3/1994 | Kuroiwa |
| 5,511,418 A | 4/1996 | Antikainen |
| 5,709,792 A | 1/1998 | Zdanevitch |
| 5,777,206 A | 7/1998 | Zuchner |
| 5,987,963 A | 11/1999 | Stormbom |
| 6,165,347 A | 12/2000 | Warburton |
| 6,320,388 B1 | 11/2001 | Sun |
| 6,338,266 B1 | 1/2002 | Warburton |
| 6,356,087 B1 | 3/2002 | Wallrafen |
| 6,435,003 B1 | 8/2002 | Warburton |
| 6,455,319 B1 | 9/2002 | Lewis |
| 6,471,838 B1 | 10/2002 | Igel |
| 6,571,603 B1 | 6/2003 | Doleman |
| 6,596,236 B2 | 7/2003 | DiMeo |
| 6,640,626 B2 | 11/2003 | Saikalis |
| 6,691,582 B1 | 2/2004 | Nawa |
| 6,787,047 B1 | 9/2004 | Hahn |
| 6,815,211 B1 | 11/2004 | Blazewicz |
| 6,895,338 B2 | 5/2005 | Hsiung |
| 6,921,883 B2 | 7/2005 | Kato |
| 7,160,690 B2 | 1/2007 | Orser |
| 7,200,495 B2 | 4/2007 | Desai |
| 7,228,725 B2 | 6/2007 | Salter |
| 7,323,343 B2 | 1/2008 | Cox |
| 7,449,146 B2 | 11/2008 | Rakow |
| 7,556,774 B2 | 7/2009 | Rakow |
| 7,680,607 B1 | 3/2010 | Smulko |
| 7,767,143 B2 | 8/2010 | Wendland |
| 7,816,681 B2 | 10/2010 | Moon |
| 7,906,233 B2 | 3/2011 | Wang |
| 2002/0098119 A1 | 7/2002 | Goodman |
| 2002/0142478 A1 | 10/2002 | Wado |
| 2003/0020494 A1 | 1/2003 | Desmier |
| 2003/0166296 A1 | 9/2003 | Morrison |
| 2003/0235817 A1 | 12/2003 | Bartkowiak |
| 2005/0014179 A1 | 1/2005 | Karlsson |
| 2005/0045493 A1 | 3/2005 | Mahurin |
| 2005/0100475 A1 | 5/2005 | Centanni |
| 2005/0148003 A1 | 7/2005 | Keith |
| 2006/0078960 A1 | 4/2006 | Hunter |
| 2006/0246273 A1 | 11/2006 | McKeown |
| 2006/0249402 A1 | 11/2006 | Snow |
| 2007/0060811 A1 | 3/2007 | Roberts |
| 2007/0118027 A1 | 5/2007 | Baker |
| 2007/0140907 A1 | 6/2007 | Rakow |
| 2007/0141580 A1 | 6/2007 | David |
| 2007/0177130 A1 | 8/2007 | MacIntyre |
| 2007/0190637 A1 | 8/2007 | Samsoondar |
| 2007/0299617 A1 | 12/2007 | Willis |
| 2008/0063575 A1 | 3/2008 | Rakow |
| 2008/0086273 A1 | 4/2008 | Shults |
| 2008/0137066 A1 | 6/2008 | Weinstein |
| 2008/0270039 A1 | 10/2008 | Dunn |
| 2008/0288182 A1 | 11/2008 | Cline |
| 2008/0312859 A1 | 12/2008 | Skyggebjerg |
| 2009/0018426 A1 | 1/2009 | Markle |
| 2009/0076360 A1 | 3/2009 | Brister |
| 2009/0112478 A1 | 4/2009 | Mueller, Jr. |
| 2009/0126460 A1 | 5/2009 | Gardner |
| 2009/0192745 A1 | 7/2009 | Kamath |
| 2009/0283421 A1 | 11/2009 | Farangis |
| 2010/0189600 A1 | 7/2010 | Hulteen |
| 2010/0277740 A1 | 11/2010 | Hulteen |
| 2010/0325073 A1 | 12/2010 | Haick |
| 2011/0031983 A1 | 2/2011 | David |
| 2011/0045601 A1 | 2/2011 | Gryska |
| 2013/0088244 A1 | 4/2013 | Gryska |
| 2013/0186177 A1 | 7/2013 | Palazzotto |
| 2013/0229194 A1 | 9/2013 | Palazzotto |

FOREIGN PATENT DOCUMENTS

| | | |
|---|---|---|
| EP | 1030174 | 8/2000 |
| EP | 2009432 | 12/2008 |
| JP | 59-206754 A | 11/1984 |
| JP | 6-281610 | 10/1994 |
| WO | WO 99-08105 | 2/1999 |
| WO | WO 99-29230 | 6/1999 |
| WO | WO 01-07121 | 1/2001 |
| WO | WO 01-81890 | 11/2001 |
| WO | WO 02-39103 | 5/2002 |
| WO | WO 03-029800 | 4/2003 |
| WO | WO 03-063699 | 8/2003 |
| WO | WO 2005-012397 | 2/2005 |
| WO | WO 2006-099518 | 9/2006 |
| WO | WO 2007-009268 | 1/2007 |
| WO | WO 2007-029033 | 3/2007 |
| WO | WO 2008-002743 | 1/2008 |
| WO | WO 2008-077745 | 7/2008 |
| WO | WO 2009-001065 | 12/2008 |
| WO | WO 2009-001070 | 12/2008 |
| WO | WO 2009-045733 | 4/2009 |
| WO | WO 2009-046011 | 4/2009 |
| WO | WO 2009-053981 | 4/2009 |
| WO | WO 2010-075333 | 7/2010 |
| WO | WO 2010-088088 | 8/2010 |
| WO | WO 2010-117599 | 10/2010 |
| WO | WO 2010-135413 | 11/2010 |
| WO | WO 2012-050686 | 4/2012 |
| WO | WO 2012-141883 | 10/2012 |
| WO | WO 2012-141894 | 10/2012 |
| WO | WO 2012-141925 | 10/2012 |
| WO | WO 2012-141958 | 10/2012 |
| WO | WO 2012-170248 | 12/2012 |
| WO | WO 2012-174099 | 12/2012 |
| WO | WO 2013-090188 | 6/2013 |

OTHER PUBLICATIONS

Budd, "Free volume and intrinsic microporosity in polymers", J. Mater. Chem., 2005, vol. 15, pp. 1977-1986.

Budd, "Solution-Processed, Organophilic Membrane Derived from a Polymer of Intrinsic Microporosity", Advanced Materials, Mar. 2004, vol. 16, No. 5, pp. 456-459.

Carta, "Novel Spirobisindanes for use as precursors to polymers of intrinsic microporosity", Organic Letters, 2008, vol. 10, No. 13, pp. 2641-2643.

Dai, "A capacitive humidity sensor integrated with micro heater and ring oscillator circuit fabricated by CMOS-MEMS technique", Sensors and Actuators B Chemical, 2007, vol. 122, pp. 375-380.

Endres, "A gas sensor system with dielectric and mass sensors", Sensors and Actuators B Chemical, Jan. 1992, vol. 6, No. 1-3, pp. 285-288.

Furjes, "Porous silicon-based humidity sensor with interdigital electrodes and internal heaters", Sensors and Actuators B Chemical, Oct. 2003, vol. 95, No. 1-3, pp. 140-144.

Ghanem, "High-Performance Membranes from Polyimides with Intrinsic Microporosity", Adv. Mater., Jul. 17, 2008, vol. 20, No. 14, pp. 2766-2771.

Ghanem, "Polymers of Intrinsic Microporosity Derived from Bis(phenazyl) Monomers", Macromolecules, 2008, vol. 41, No. 5, pp. 1640-1646.

Matsuguchi, "Capacitive-Type Humidity Sensors Using Polymerized Vinyl Carboxylate", J. Electrochemical Soc., Mar. 1994, vol. 141, No. 3, pp. 614-618.

McKeown, "Polymers of Intrinsic Microporosity (PIMs): Bridging the Void between Microporous and Polymeric Materials", Chem. Eur. J., 2005, vol. 11, No. 9, pp. 2610-2620.

Patel, "Chemicapacitive Microsensors for Volatile Organic Compound Detection", Sensors and Actuators B Chemical, Dec. 1, 2003, vol. 96, No. 3, pp. 541-553. XP004475577.

(56) References Cited

OTHER PUBLICATIONS

Smiths Detection, The Cyranose 320 E Nose User's Manual 11-6001, Edition 5, 2000, 102 pages.

International Search Report for PCT International Application No. PCT/US2012/032153, Mailed on Jul. 6, 2012, 4 pages.

Co-pending U.S. Appl. No. 14/007,144 entitled "Electronic Device Including Calibration Information and Method of Using the Same", Pallazzotto et al., filed Sep. 24, 2013.

Co-pending U.S. Appl. No. 14/007,106, entitled "Method of Using an Absorptive Sensor Element", Pallazzotto et al., filed Sep. 24, 2013.

Co-pending U.S. Appl. No. 14/007,230, entitled "Method of Detecting Volatile Organic Compounds", Kang et al., filed Sep. 24, 2013.

US 9,506,888 B2

VAPOR SENSOR INCLUDING SENSOR ELEMENT WITH INTEGRAL HEATING

FIELD

The present disclosure broadly relates to vapor sensors.

BACKGROUND

The presence of vapors, and their concentration in air, is monitored in many fields of endeavor. Various methods for detecting vapors (e.g., volatile organic compounds (VOCs)) have been developed including, for example, photoionization, gas chromatography, gravimetric techniques, spectroscopic techniques (e.g., mass spectrometry, infrared spectroscopy, or fluorescence spectroscopy), and absorptive sensing techniques.

In capacitance sensors, the capacitance of two conductive electrodes (typically parallel or interdigitated), varies as the dielectric constant of material between the two electrodes changes due to the presence of an environmental analyte vapor. Periodically, it is desirable to remove the analyte from between the conductive electrodes (for example, if switching analyte vapors). In such instances, heating can be used to evaporate the analyte prior to use of the capacitance sensor.

SUMMARY

In one aspect, the present disclosure provides a vapor sensor comprising:
  a capacitance-related property sensor element, the capacitance-related property sensor element comprising:
    a dielectric substrate;
    a first conductive electrode disposed on the dielectric substrate, the first conductive electrode having first and second ends;
    a second conductive electrode; and
    a dielectric layer comprising a microporous material disposed between and contacting the first conductive electrode and the second conductive electrode;
  a heater circuit element having first and second conductive members, wherein the first and second conductive members are in reversibly interruptible electrical communication with the first and second ends of the first conductive electrode, respectively;
  a capacitance-related property measurement circuit element, the capacitance-related property measurement circuit element having first and second conductive members, wherein the first conductive member of the capacitance-related property measurement circuit element is in reversibly interruptible electrical communication with the first conductive electrode, and wherein the second conductive member of the capacitance-related property measurement circuit element is in electrical communication with the second conductive electrode;
  at least one switch member, wherein said at least one switch member is capable of reversibly interrupting the electrical communication between the first and second conductive members of the heater circuit element to the respective first and second ends of the first conductive electrode, wherein said at least one switch member is capable of reversibly interrupting the electrical communication between the first conductive member of the capacitance-related property measurement circuit element to the first conductive electrode.

In some embodiments, the first and second conductive electrodes and the detection layer each contact the substrate. In some embodiments, the first and second conductive electrodes are parallel.

In some embodiments, said at least one switch member is capable of simultaneously reversibly interrupting:
  the reversibly interruptible electrical communication between the first and second conductive members of the heater circuit element to the respective first and second ends of the first conductive electrode; and
  the reversibly interruptible electrical communication between the first conductive member of the capacitance-related property measurement circuit element to the second conductive electrode, respectively.

In some embodiments, the vapor sensor further comprises a temperature sensor disposed on the dielectric substrate proximate the first conductive electrode.

In some embodiments, the vapor sensor further comprises a switch controller, wherein the switch controller is in electrical communication with the switch member and controls operation of the switch. In some of those embodiments, the switch controller is in electrical communication with the temperature sensor.

Vapor sensors according to the present disclosure are useful, for example to measure concentrations of analyte (e.g., volatile organic compounds and/or humidity).

Advantageously, in vapor sensors according to the present disclosure, the first conductive electrode doubles in capacitance-related property sensing and as a heating element, thereby eliminating the need for an additional heating element and simplifying design and fabrication of the vapor sensor.

Sensor elements used in practice of the present disclosure are generally configured such that the absorptive dielectric layer is in sufficiently close proximity to the first conductive electrode and the second conductive electrode that the absorptive dielectric material contained in the layer will be capable of interacting with an electric field that is established by the electrodes. In operation of the sensor element, the absorptive dielectric layer exhibits a change in an electrical property upon absorption of one or more analytes (e.g., one or more organic vapors). The electrical property may be a capacitance-related property as described below. Such a change in a capacitance-related property can be measured by imparting a charge differential between the first conductive electrode and the second conductive electrode (e.g., by imparting a voltage differential to the electrodes) and monitoring the property of the sensor element in response to the presence of the analyte.

The term "capacitance-related property" encompasses any electrical property and the measurement thereof that is in general associated with the imparting of an electrical charge (whether static or time variant) and the monitoring of an electrical property during and/or after the imparting of the charge. Such properties include, for example, not only capacitance, but also impedance, inductance, admittance, current, resistance, conductance, etc., and may be measured according to various methods known in the art.

As used herein, the term "absorb" refers to material becoming disposed within the dielectric microporous material, regardless of whether it is merely adsorbed to the pore walls, or dissolved into the bulk dielectric microporous material.

As used herein, the term "permeable" in reference to a layer of a material (e.g., a conductive electrode) means that in areas where the layer is present, the layer is sufficiently porous to be non-reactively permeable through its thickness (e.g., at 25° C.) by at least one organic compound.

As used herein, the term "conductive member" refers to an electrically conductive member such as, for example, a wire, a metallic trace, electrical component, or a combination thereof.

The features and advantages of the present disclosure will be further understood upon consideration of the detailed description as well as the appended claims.

While the above-identified drawing figures set forth several embodiments of the present disclosure, other embodiments are also contemplated, as noted in the discussion. It should be understood that numerous other modifications and embodiments can be devised by those skilled in the art, which fall within the scope and spirit of the principles of the disclosure. The figures may not be drawn to scale. Like reference numbers may have been used throughout the figures to denote like parts.

DETAILED DESCRIPTION

Vapor sensors suitable for use in the present disclosure may include various sensor element configurations.

Figure 1:
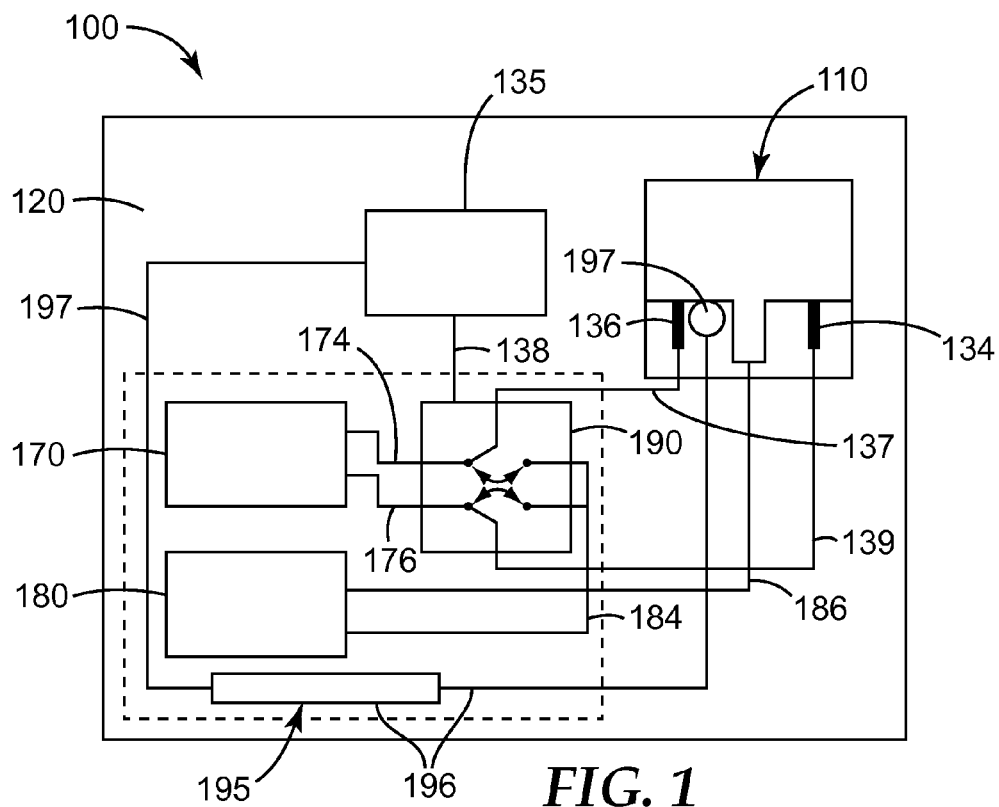
FIG. 1 is a schematic plan view of an exemplary vapor sensor 100 according to the present disclosure.
Figure 2:
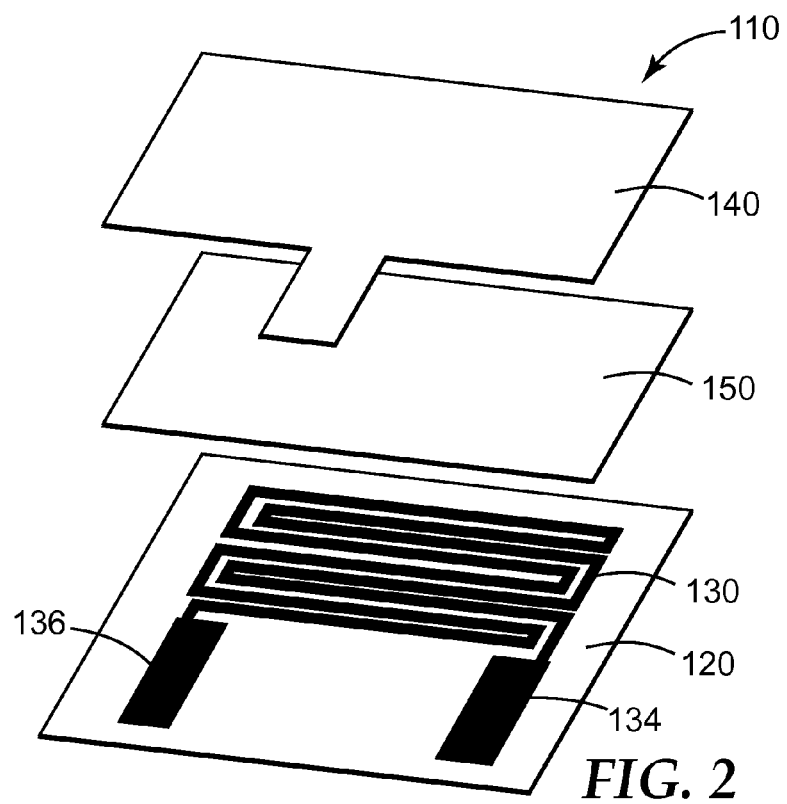
FIG. 2 is a schematic exploded perspective view of sensor element 110 shown in FIG. 1.

In one embodiment, shown in FIG. 1 the vapor sensor includes a sensor element having a layered electrode configuration. Referring now to FIG. 1, exemplary vapor sensor 100 according to the present disclosure comprises capacitance-related property sensor element 110. As shown in FIG. 2, capacitance-related property sensor element 110 comprises: dielectric substrate 120; first conductive electrode 130 disposed on dielectric substrate 120; second conductive electrode 140; and layer of dielectric microporous material 150 disposed between and contacting first conductive electrode 130 and second conductive electrode 140.

Dielectric substrate 120 may comprise, for example, a continuous slab, layer, or film of dielectric material. It is disposed in sufficient proximity to the first conductive electrode 130 that it may serve to provide physical strength and integrity to the sensor element. Any suitable dielectric material may be used, including, for example, glass, ceramic, and/or plastic. In large scale production, a polymeric film (such as polyester or polyimide) may be used.

First conductive electrode 130 can comprise any suitable conductive material. Combinations of different materials (conductive and/or nonconductive) can be used, as different layers or as a mixture, as long as sufficient overall conductivity is provided. Typically, first conductive electrode 130 has a sheet resistance of less than about $10^7$ ohms/square. Examples of materials that can be used to make first conductive electrode 130 and/or second conductive electrode 140 include, but are not limited to, organic materials, inorganic materials, metals, alloys, and various mixtures and composites comprising any or all of these materials. In certain embodiments, coated (for example, thermal vapor coated or sputter coated) metals or metal oxides, or combinations thereof, may be used. Suitable conductive materials include for example aluminum, nickel, titanium, tin, indium-tin oxide, gold, silver, platinum, palladium, copper, chromium, carbon nanotubes, and combinations thereof. In certain embodiments, first conductive electrode 130 may also be formed by printing a metallic ink (e.g., a silver ink or a gold ink), followed by drying the ink. First conductive electrode 130 has respective first and second ends 134, 136.

Second conductive electrode 140 may include any material(s) as long as it remains permeable by at least one organic analyte. Examples of materials that can be used to make second conductive electrode 140 include organic materials, inorganic materials, metals, alloys, and various mixtures and composites comprising any or all of these materials. In certain embodiments, coated (for example, thermal vapor coated, sputter coated, etc.) metals or metal oxides, or combinations thereof, may be used. Suitable conductive materials include for example aluminum, nickel, titanium, tin, indium-tin oxide, gold, silver, platinum, palladium, copper, chromium, carbon nanotubes, and combinations thereof. Details concerning vapor deposited vapor permeable conductive electrodes can also be found in U.S. Provisional Patent Appln. No. 61/388,146 (Palazzotto et al.), the disclosure of which is incorporated herein by reference.

In certain embodiments, second conductive electrode 140 may also be formed by printing a metallic ink (e.g., a silver ink or a gold ink), followed by drying the ink. Combinations of different materials (conductive and/or nonconductive) can be used, as different layers or as a mixture, as long as sufficient overall conductivity and permeability is provided. Typically, second conductive electrode 140 has a sheet resistance of less than about $10^7$ ohms/square. As shown in FIG. 2, second conductive electrode 140 is configured as a rectangular electrode that extends beyond the perimeter of first conductive electrode 130; other configurations may also be used. For example, the shape of second conductive electrode 140 may be similar to, or substantially the same as, first conductive electrode 130.

Conductive members 137, 139 electrically connect respective second end 136 and first end 134 of first conductive electrode 130 to switch member 190, such that in one switch configuration a closed circuit is formed that includes first conductive electrode 130 and capacitance-related property measurement circuit element 180.

Figure 3:
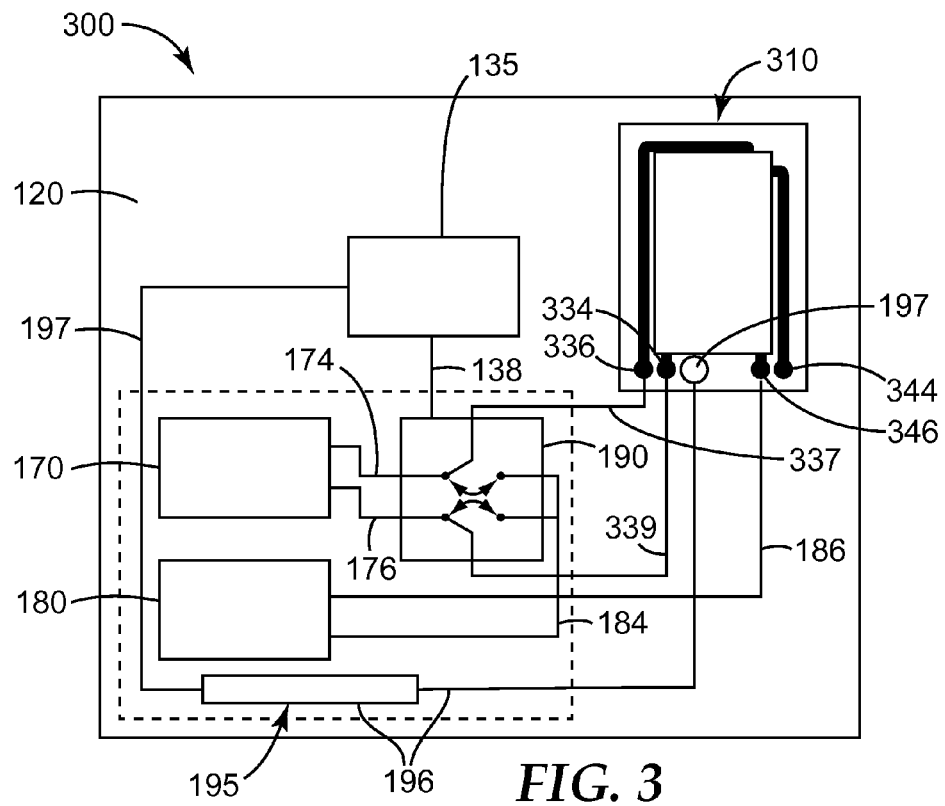
FIG. 3 is a schematic plan view of an exemplary vapor sensor 300 according to the present disclosure.

In a second embodiment, shown in FIG. 3 the vapor sensor includes a sensor element having a side-by-side electrode configuration. Referring now to FIG. 3, exemplary vapor sensor 300 according to the present disclosure comprises capacitance-related property sensor element 310.

Figure 4:
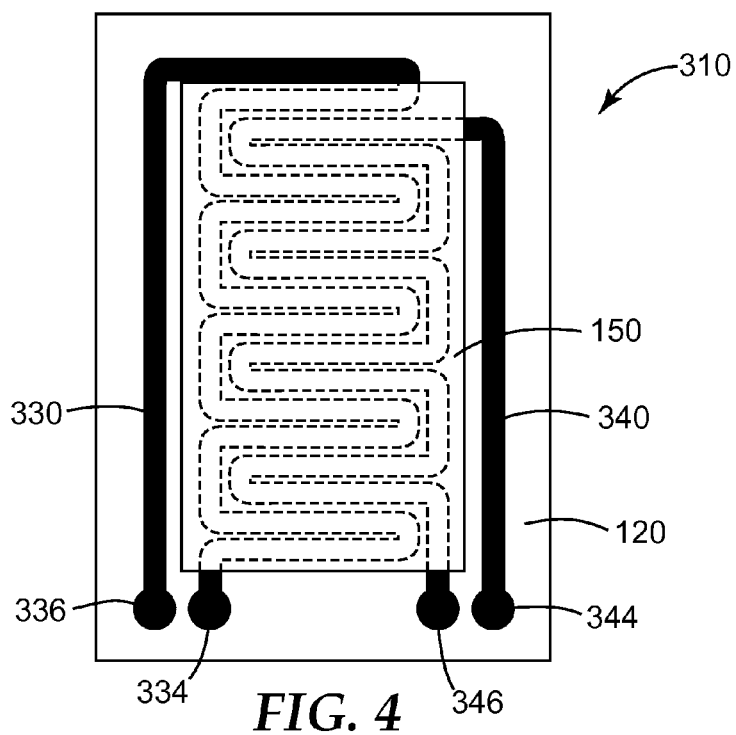
FIG. 4 is a schematic plan view of sensor element 310 shown in FIG. 3.

As shown in FIG. 4, capacitance-related property sensor element 310 comprises: dielectric substrate 120; first conductive electrode 330 disposed on dielectric substrate 120; second conductive electrode 340; and layer of dielectric microporous material 150 disposed between and contacting first conductive electrode 330 and second conductive electrode 340. First conductive electrode 330 has respective first and second ends 334, 336. Conductive member 337 electrically connects second end 336 to switch member 190, such that in one switch configuration a closed circuit is formed that includes first conductive electrode 330 and capacitance-related property measurement circuit element 180.

First conductive electrode 330 can comprise any suitable conductive material. Combinations of different materials (conductive and/or nonconductive) can be used, as different layers or as a mixture, as long as sufficient overall conductivity is provided. Typically, first conductive electrode 330 has a sheet resistance of less than about $10^7$ ohms/square. Examples of materials that can be used to make first conductive electrode 330 and/or second conductive electrode 340 include, but are not limited to, organic materials, inorganic materials, metals, alloys, and various mixtures and composites comprising any or all of these materials. In certain embodiments, coated (for example, thermal vapor coated or sputter coated) metals or metal oxides, or combinations thereof, may be used. Suitable conductive materials include for example aluminum, nickel, titanium, tin, indium-tin oxide, gold, silver, platinum, palladium, copper, chromium, carbon nanotubes, and combinations thereof. In certain embodiments, first conductive electrode 330 may also be formed by printing a metallic ink (e.g., a silver ink or a gold ink), followed by drying the ink.

In the configuration shown in FIG. 4, second conductive electrode 340 need not be permeable by an organic analyte, although it may be, if desired. Examples of materials that can be used to make second conductive electrode 340 include organic materials, inorganic materials, metals, alloys, and various mixtures and composites comprising any or all of these materials. In certain embodiments, coated (for example, thermal vapor coated, sputter coated, etc.) metals or metal oxides, or combinations thereof, may be used. Suitable conductive materials include for example aluminum, nickel, titanium, tin, indium-tin oxide, gold, silver, platinum, palladium, copper, chromium, carbon nanotubes, and combinations thereof. In certain embodiments, second conductive electrode 340 may also be formed by printing a metallic ink (e.g., a silver ink or a gold ink), followed by drying the ink. Combinations of different materials (conductive and/or nonconductive) can be used, as different layers or as a mixture, as long as sufficient overall conductivity and permeability is provided. Typically, second conductive electrode 340 has a sheet resistance of less than about $10^7$ ohms/square.

The first conductive electrode can be of any thickness as long as it is conductive; for example, in a thickness in a range of from at least 4 nanometers (nm) to 400 nm, or from 10 nm to 200 nm.

The first conductive electrode may follow a tortuous path; for example, as shown in FIGS. 2 and 4; however, this is not a requirement, and other configurations are also contemplated. A tortuous path typically serves to increase the area that may be heated and/or increase the rate of heating. In general, the design of first conductive electrode should allow for facile resistive heating when in electrical communication with the heater circuit element. Such design considerations are within the skill level of one of ordinary skill in the art.

The second conductive electrode typically has a thickness in a range of from 1 nm to 100 micrometers, although other thicknesses may be used.

For example, in the embodiment shown in FIG. 2, the second conductive electrode may have a thickness in a range of from 1 nm to 100 nm, or even from 4 nm to 10 nm nanometers. Greater thicknesses may have undesirably low levels of permeability, while lesser thicknesses may become insufficiently conductive and/or difficult to electrically connect to the second conductive member.

In the embodiment shown in FIG. 4, the first and second electrodes may be disposed side-by-side on the surface of the dielectric substrate (e.g., within a single plane), separated by the absorptive intrinsically porous material. In this embodiment, the second conductive electrode need not be permeable by the analyte vapor. In such a case, the second conductive electrode may be fabricated using a material suitable for use as the first conductive electrode.

Dielectric microporous material 150 can be any material that is microporous and is capable of absorbing at least one analyte within its interior. In this context, the terms "microporous" and "microporosity" mean that the material has a significant amount of internal, interconnected pore volume, with the mean pore size (as characterized, for example, by sorption isotherm procedures) being less than about 100 nm, typically less than about 10 nm. Such microporosity provides that molecules of organic analyte (if present) will be able to penetrate the internal pore volume of the material and take up residence in the internal pores. The presence of such analyte in the internal pores can alter the dielectric properties of the material such that a change in the dielectric constant (or any other suitable electrical property) can be observed.

In some embodiments, the dielectric microporous material comprises a so-called Polymer of Intrinsic Microporosity (PIM). PIMs are polymeric materials with nanometer-scale pores due to inefficient packing of the polymer chains. For example, in *Chemical Communications*, 2004, (2), pp. 230-231, Budd et al. report a series of intrinsically microporous materials containing dibenzodioxane linkages between rigid and/or contorted monomeric building blocks. Representative members of this family of polymers include those generated by condensation of Component A (e.g., A1, A2, or A3) with Component B (e.g., B1, B2, or B3) as shown in Table 1 according to Scheme 1.

SCHEME 1

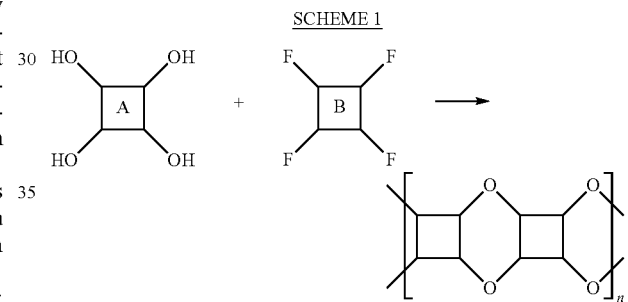

TABLE 1

COMPONENT A

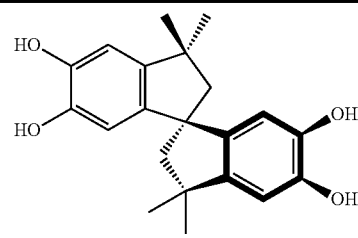

A1

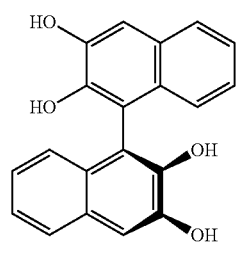

A2

TABLE 1-continued

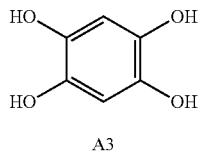

A3

COMPONENT B

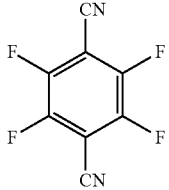 [SMILES: N#Cc1c(F)c(F)c(C#N)c(F)c1F]

B1

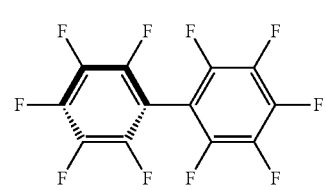

B2

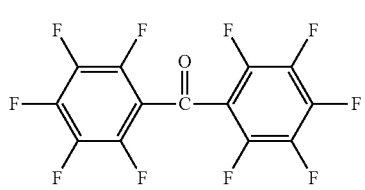 [SMILES: O=C(c1c(F)c(F)c(F)c(F)c1F)c1c(F)c(F)c(F)c(F)c1F]

B3

Further suitable Components A and B, and resultant intrinsically microporous polymers, are known in the art, for example, as reported by Budd et al. in *Journal of Materials Chemistry*, 2005, Vol. 15, pp. 1977-1986; by McKeown et al. in *Chemistry, A European Journal*, 2005, Vol. 11, pp. 2610-2620; by Ghanem et al. in *Macromolecules*, 2008, vol. 41, pp. 1640-1646; by Ghanem et al. in *Advanced Materials*, 2008, vol. 20, pp. 2766-2771; by Carta et al. in *Organic Letters*, 2008, vol. 10 (13), pp. 2641-2643; in PCT Published Application WO 2005/012397 A2 (McKeown et al.); and in U.S. Patent Appl. Publ. No. 2006/0246273 (McKeown et al.), the disclosure of which is incorporated herein by reference.

Such polymers can be synthesized, for example, by a step-growth polymerization where a bis-catechol such as, e.g., A1 (5,5',6,6'-tetrahydroxy-3,3,3',3'-tetramethyl-1,1'-spirobisindane) is allowed to react with a fluorinated arene such as, e.g., B1 (tetrafluoroterephthalonitrile) under basic conditions. Due to the rigidity and contorted nature of the backbone of the resulting polymers, these polymers are unable to pack tightly in the solid state and thus have at least 10 percent free volume and are intrinsically microporous.

PIMs may be blended with other materials. For example, a PIM may be blended with a material that itself is not an absorptive dielectric material. Even though not contributing to an analyte response, such a material may be useful for other reasons. For example, such a material may allow the formation of a PIM-containing layer which has superior mechanical properties and the like. In one embodiment, PIMs may be dissolved in a common solvent with the other material to form a homogeneous solution, which may be cast to form an absorptive dielectric blend layer comprising both the PIM and the other polymer(s). PIMs may also be blended with a material that is an absorptive dielectric material (for example, zeolites, activated carbon, silica gel, hyper-crosslinked polymer networks and the like). Such materials may comprise insoluble materials that are suspended in a solution comprising of a PIMs material. Coating and drying of such a solution/suspension may provide a composite absorptive dielectric layer comprising both the PIM material and the additional absorptive dielectric material.

PIMs are typically soluble in organic solvents such as, for example, tetrahydrofuran and can thus be cast as films from solution (e.g., by spin-coating, dip coating, or bar coating). However, characteristics (accessible thicknesses, optical clarity, and/or appearance) of films made from solutions of these polymers may vary markedly depending on the solvent or solvent system used to cast the film. For example, intrinsically microporous polymers of higher molecular weights may need to be cast from relatively unusual solvents (e.g., cyclohexene oxide, chlorobenzene, or tetrahydropyran) to generate films with desirable properties for use in vapor sensors as described herein. In addition to solution coating methods, the detection layer may be applied to the first conductive electrode by any other suitable method.

After a PIM is deposited (e.g., coated) or otherwise formed so as to comprise an absorptive dielectric layer, the material may be crosslinked using a suitable crosslinking agent such as, for example, bis(benzonitrile)palladium(II) dichloride. This process may render the absorptive dielectric layer insoluble in organic solvents, and/or may enhance certain physical properties such as durability, abrasion resistance, etc., which may be desirable in certain applications.

PIMs may be hydrophobic so that they will not absorb liquid water to an extent that the material swells significantly or otherwise exhibits a significant change in a physical property. Such hydrophobic properties are useful in providing an organic analyte sensor element that is relatively insensitive to the presence of water. The material may however comprise relatively polar moieties for specific purposes.

In one embodiment, the dielectric microporous material comprises a continuous matrix. Such a matrix is defined as an assembly (e.g., a coating, layer, etc.) in which the solid portion of the material is continuously interconnected (irrespective of the presence of porosity as described above, or of the presence of optional additives as discussed below). That is, a continuous matrix is distinguishable from an assembly that comprises an aggregation of particles (e.g., zeolites, activated carbons, carbon nanotubes, etc.). For example, a layer or coating deposited from a solution will typically comprise a continuous matrix (even if the coating itself is applied in a patterned manner and/or comprises particulate additives). A collection of particles deposited via powder spraying, coating and drying of a dispersion (e.g., a latex), or by coating and drying of a sol-gel mixture, may not comprise a continuous network. However, if such a latex, sol-gel, etc., layer can be consolidated such that individual particles are no longer discernible, nor is it possible to discern areas of the assembly that were obtained from different particles, such a layer may then be considered to be a continuous matrix.

Capacitance-related property sensor elements according to the present disclosure can be made, for example, by disposing the first conductive electrode on the dielectric substrate (e.g., by vapor deposition or by photolithography) using a method common in circuit manufacture (e.g., by vapor deposition or by photolithography).

Next, dielectric microporous material in a suitable organic solvent is coated onto the first conductive electrode and the solvent removed. Finally, the second conductive electrode is disposed on the dielectric microporous material (e.g., by vapor deposition or a printing method such as screen printing, using a digital printing method (e.g., ink jet printing)).

Referring again to FIGS. 1 and 3, heater circuit element 170 has respective first and second conductive members 174, 176. The first and second conductive members are in reversibly interruptible electrical communication with the first and second ends (134, 136 or 334, 336) of first conductive electrode (130 or 330), respectively. The heater circuit element s upplies electrical power to the first conductive electrode, causing it to rise in temperature due to resistive heating. The heater circuit element should be selected such that it is readily able to supply sufficient electrical power to heat the first conductive electrode. Examples of heater circuit elements include alternating current (ac) adapters (if connected to a power source) and batteries.

In the embodiment shown in FIG. 1, capacitance-related property measurement circuit element 180 has first conductive member 184 in reversibly interruptible electrical communication with first and second ends 134, 136 of first conductive electrode 130 via switch member 190 and conductive traces 139, 137, respectively.

In the embodiment shown in FIG. 3, capacitance-related property measurement circuit element 180 has first conductive member 184 in reversibly interruptible electrical communication with first and second ends 334, 336 of first conductive electrode 330 via switch member 190 and conductive traces 339, 337, respectively.

Any device capable of measuring a capacitance-related property can be used as capacitance-related property measurement circuit element 180. Examples include LCR meters and microprocessors (e.g., in combination with a digitizer).

As shown in FIGS. 1 and 3, second conductive member 186 is in electrical communication with the second conductive electrode (140 or 340, respectively). However, it is also contemplated that vapor sensors according to the present disclosure may be configured such that the second conductive member is in reversibly interruptible electrical communication with the second conductive electrode. The capacitance-related property measurement circuit element may be communicatively coupled to a microprocessor, display, or other device.

In some embodiments, the second conductive electrode may have first and second ends. Referring now to FIG. 4, exemplary second conductive electrode 340 has respective first and second ends 344, 346. In this configuration, second conductive member 186 is in electrical communication with second conductive electrode 340 through first end 344. Optionally, second conductive member 186 may be in contact with respective first and second ends 344, 346. It is further contemplated that sensor elements such as, for example, that shown in FIG. 4 can be configured to have the heater circuit element in reversibly interruptible electrical communication with the first and second conductive electrodes via one or more switch members.

The capacitance-related property measurement circuit element applies a voltage difference between the first conductive electrode and the second conductive electrode and measures a capacitance-related property. This capacitance-related property is then used, for example, whether by hand or by microprocessor to obtain the vapor concentration for a known analyte; for example, according to a reference calibration. One exemplary method of determining the vapor concentration of an analyte vapor is disclosed in U.S. Provisional Patent Appl. No. 61/475,014, entitled "ELECTRONIC DEVICE INCLUDING CALIBRATION INFORMATION AND METHOD OF USING THE SAME", filed Apr. 13, 2011.

Referring again to FIGS. 1 and 3, switch member 190 is capable of simultaneously reversibly interrupting the electrical communication between the first and second conductive members (174, 176) of heater circuit element 170 to the respective first and second ends of the first conductive electrode (e.g., first conductive electrode 130 or first conductive electrode 330), and reversibly interrupting the electrical communication between the first and second conductive members of the capacitance-related property measurement circuit element to the first conductive electrode and the second conductive electrode. Conductive member 137 or 337 electrically connects second end 136 or 336 of respective first conductive electrode 130 or 330, to switch member 190.

In the embodiments shown in FIGS. 1 and 3, a single switch member is included; however, other configurations involving more switch members are also contemplated. For example, each of the heater circuit element and the capacitance-related property circuit element may be connected to the sensor element by separate switch members. However, in terms of convenience, the embodiments shown in FIGS. 1 and 3 are advantageous.

The switch member regulates whether a) current flows to through the first conductive electrode from its first end to the second end, or b) whether the capacitance-related circuit measurement circuit element is in electrical communication with the first conductive electrode and the second conductive electrode. In mode a) heating of the sensor element is achieved, while in mode b) capacitance-related property measurement element may be obtained. Simultaneous heating of the first conductive electrode and capacitance-related property measurement is also envisaged.

Suitable switch members include, for example, digital and analog switches. In addition, more than one switch member (independently of any type) may be included in the vapor sensor. Examples include electromechanical switches such as toggle switches, in-line switches, push-button switches, rocker switches, and keypad switches, and electrical switches such as transistor-based semiconductor switches. Desirably, any switch member(s) is/are electrically operable.

Optional switch controller 135 is in electrical communication with switch member 190, via conductive member 138 and controls the operation of switch member 190. Examples of suitable optional switch controllers include semiconductor microprocessors and computers.

Referring again to FIGS. 1 and 3, optional temperature sensor 195 includes temperature measurement circuit element 196 and probe 197. Probe 197 is disposed on the dielectric substrate proximate the first conductive electrode (110 or 310), in order to permit measurement of the capacitance-related property sensor element temperature. Examples of suitable optional temperature sensors include thermocouples and thermistors. If present, optional temperature sensor 195 may be electrically connected to via conductive trace 197 to optional switch controller 135 that monitors temperature and controls connections through switch member(s). For example, it may regulate the on-off duty cycle of heating and capacitance-related property measurement such that a desired temperature is achieved.

Further components that may be included in vapor sensors according to the present disclosure include a partial cover, an electronic display, and computer-readable memory.

While not explicitly shown, it will be understood that the various electrical components of vapor sensors according to the present disclosure are supplied with sufficient electrical power to function during use.

An optional protective cover or barrier layer can be provided in proximity to at least one of the first or second conductive electrodes. For example, in one embodiment, a cover layer can be placed atop the second conductive electrode, leaving an area of second conductive electrode accessible for electrical contact with the second conductive member electrical contact. Any such cover layer should not significantly interfere with the functioning of sensor element. For example, if the sensor element is configured such that an analyte of interest must pass through cover layer in order to reach the absorptive dielectric layer, the cover layer should be sufficiently permeable by the analyte.

SELECT EMBODIMENTS OF THE PRESENT DISCLOSURE

In a first embodiment, the present disclosure provides a vapor sensor comprising:
  a capacitance-related property sensor element, the capacitance-related property sensor element comprising:
    a dielectric substrate;
    a first conductive electrode disposed on the dielectric substrate, the first conductive electrode having first and second ends;
    a second conductive electrode; and
    a dielectric layer comprising a microporous material disposed between and contacting the first conductive electrode and the second conductive electrode;
  a heater circuit element having first and second conductive members, wherein the first and second conductive members are in reversibly interruptible electrical communication with the first and second ends of the first conductive electrode, respectively;
  a capacitance-related property measurement circuit element, the capacitance-related property measurement circuit element having first and second conductive members, wherein the first conductive member of the capacitance-related property measurement circuit element is in reversibly interruptible electrical communication with the first conductive electrode, and wherein the second conductive member of the capacitance-related property measurement circuit element is in electrical communication with the second conductive electrode;
  at least one switch member, wherein said at least one switch member is capable of reversibly interrupting the electrical communication between the first and second conductive members of the heater circuit element to the respective first and second ends of the first conductive electrode, wherein said at least one switch member is capable of reversibly interrupting the electrical communication between the first conductive member of the capacitance-related property measurement circuit element to the first conductive electrode.

In a second embodiment, the present disclosure provides a vapor sensor according to the first embodiment, wherein said at least one switch member is capable of simultaneously reversibly interrupting:
  the reversibly interruptible electrical communication between the first and second conductive members of the heater circuit element to the respective first and second ends of the first conductive electrode; and
  the reversibly interruptible electrical communication between the first conductive member of the capacitance-related property measurement circuit element to the second conductive electrode, respectively.

In a third embodiment, the present disclosure provides a vapor sensor according to the first or second embodiment, wherein the second conductive electrode is permeable by at least one organic vapor.

In a fourth embodiment, the present disclosure provides a vapor sensor according to any one of the first to third embodiments, wherein the second conductive electrode comprises dried silver ink.

In a fifth embodiment, the present disclosure provides a vapor sensor according to any one of the first to third embodiments, wherein the second conductive electrode comprises a vapor-deposited metal.

In a sixth embodiment, the present disclosure provides a vapor sensor according to any one of the first to fifth embodiments, wherein the microporous material comprises a polymer of intrinsic microporosity.

In a seventh embodiment, the present disclosure provides a vapor sensor according to any one of the first to the sixth embodiments, further comprising a switch controller, wherein the switch controller is in electrical communication with the switch member and controls operation of the switch.

In an eighth embodiment, the present disclosure provides a vapor sensor according to any one of the first to seventh embodiments, further comprising a temperature sensor disposed on the dielectric substrate proximate the first conductive electrode.

In a ninth embodiment, the present disclosure provides a vapor sensor according to the eighth embodiment, wherein the switch controller is in electrical communication with temperature sensor.

In a tenth embodiment, the present disclosure provides a vapor sensor according to any one of the first to ninth embodiments, wherein the first and second conductive electrodes and the detection layer each contact the substrate.

In an eleventh embodiment, the present disclosure provides a vapor sensor according to any one of the first to ninth embodiments, wherein the first and second conductive electrodes are parallel.

In a twelfth embodiment, the present disclosure provides a vapor sensor according to any one of the first to eleventh embodiments, wherein the capacitance-related property comprises capacitance.

Various modifications and alterations of this disclosure may be made by those skilled in the art without departing from the scope and spirit of this disclosure, and it should be understood that this disclosure is not to be unduly limited to the illustrative embodiments set forth herein.

What is claimed is:
1. A vapor sensor comprising:
  a capacitance-related property sensor element, the capacitance-related property sensor element comprising:
    a dielectric substrate;
    a first conductive electrode disposed on the dielectric substrate, the first conductive electrode having first and second ends, and the first conductive electrode extending along a path thereof between the first and second ends; and
    a second conductive electrode;

a dielectric layer comprising a microporous material disposed between and contacting the first conductive electrode and the second conductive electrode, wherein the microporous material comprises a polymer of intrinsic microporosity;

a heater circuit element having first and second conductive members, wherein the first and second conductive members are in reversibly interruptible electrical communication with the first and second ends of the first conductive electrode, respectively, such that current flows through the first conductive electrode from the first end to the second end;

a capacitance-related property measurement circuit element, the capacitance-related property measurement circuit element having first and second conductive members, wherein the first conductive member of the capacitance-related property measurement circuit element is in reversibly interruptible electrical communication with the first conductive electrode, and wherein the second conductive member of the capacitance-related property measurement circuit element is in electrical communication with the second conductive electrode; and at least one switch member, wherein said at least one switch member is capable of reversibly interrupting the electrical communication between the first and second conductive members of the heater circuit element to the respective first and second ends of the first conductive electrode, wherein said at least one switch member is capable of reversibly interrupting the electrical communication between the first conductive member of the capacitance-related property measurement circuit element to the first conductive electrode.

2. The vapor sensor of claim 1, wherein said at least one switch member is capable of simultaneously reversibly interrupting:

the reversibly interruptible electrical communication between the first and second conductive members of the heater circuit element to the respective first and second ends of the first conductive electrode; and the reversibly interruptible electrical communication between the first conductive member of the capacitance-related property measurement circuit element to the second conductive electrode, respectively.

3. The vapor sensor of claim 1, wherein the second conductive electrode is permeable by at least one organic vapor.

4. The vapor sensor of claim 1, wherein the second conductive electrode comprises dried silver ink.

5. The vapor sensor of claim 1, wherein the second conductive electrode comprises a vapor-deposited metal.

6. The vapor sensor of claim 1, further comprising a switch controller, wherein the switch controller is in electrical communication with the switch member and controls operation of the switch.

7. The vapor sensor of claim 1, further comprising a temperature sensor disposed on the dielectric substrate proximate the first conductive electrode.

8. The vapor sensor of claim 7, wherein a switch controller is in electrical communication with the temperature sensor.

9. The vapor sensor of claim 1, wherein the first and second conductive electrodes and the detection layer each contact the substrate.

10. The vapor sensor of claim 1, wherein the first and second conductive electrodes are parallel.

11. The vapor sensor of claim 1, wherein the capacitance-related property comprises capacitance.

* * * * *

UNITED STATES PATENT AND TRADEMARK OFFICE
CERTIFICATE OF CORRECTION

PATENT NO.         : 9,506,888 B2                                    Page 1 of 1
APPLICATION NO.    : 14/110047
DATED              : November 29, 2016
INVENTOR(S)        : Palazzotto et al.

It is certified that error appears in the above-identified patent and that said Letters Patent is hereby corrected as shown below:

In the Specification

Column 9
Line 16, Delete "s upplies" and insert -- supplies --, therefor.

Column 10
Line 6, Delete "61/475,014," and insert -- 61/475,014 (Attorney Docket No. 67334US002), --, therefor.

Signed and Sealed this
Twenty-eighth Day of February, 2017

Michelle K. Lee
*Director of the United States Patent and Trademark Office*